United States Patent
Bellandi et al.

(10) Patent No.: US 10,464,893 B2
(45) Date of Patent: Nov. 5, 2019

(54) DERIVATIVES OF PYRROLE-2,5-DIONES HAVING A FUNGICIDAL ACTIVITY, THEIR AGRONOMICAL COMPOSITIONS AND USE THEREOF

(71) Applicant: ISAGRO S.p.A., Milan (IT)

(72) Inventors: Paolo Bellandi, Carcare (IT); Marilena Gusmeroli, Monza (IT); Silvia Mormile, Novara (IT); Christian Badaracco, Vittuone (IT); Matteo Vazzola, Cogliate (IT)

(73) Assignee: ISAGRO S.P.A, Milan (IT)

( * ) Notice: Subject to any disclaimer, the term of this patent is extended or adjusted under 35 U.S.C. 154(b) by 0 days.

(21) Appl. No.: 16/086,771

(22) PCT Filed: Mar. 30, 2017

(86) PCT No.: PCT/IB2017/051831
§ 371 (c)(1),
(2) Date: Sep. 20, 2018

(87) PCT Pub. No.: WO2017/168368
PCT Pub. Date: Oct. 5, 2017

(65) Prior Publication Data
US 2019/0106388 A1    Apr. 11, 2019

(30) Foreign Application Priority Data
Mar. 31, 2016   (IT) .................. 102016000033341

(51) Int. Cl.
C07D 207/50    (2006.01)
C07D 207/48    (2006.01)
A01N 43/36     (2006.01)
A01N 47/18     (2006.01)

(52) U.S. Cl.
CPC ........... C07D 207/50 (2013.01); A01N 43/36 (2013.01); A01N 47/18 (2013.01); C07D 207/48 (2013.01)

(58) Field of Classification Search
CPC ...... A01N 43/36; A01N 47/18; C07D 207/10; C07D 207/48
See application file for complete search history.

(56) References Cited

FOREIGN PATENT DOCUMENTS

CN    101538256    *    5/2014

OTHER PUBLICATIONS

Guan Qi, et al: "Microwave-assisted synthesis and biological evaluation of 3,4-diaryl maleic anhydride/N-substituted maleimide derivatives as combretastatin A-4 analogues", Bioqrganic & Medicinal Chemistry Letters, vol. 25, No. 3, Dec. 8, 2014 (Dec. 8, 2014), pp. 631-634.

M. Sortino et al: "Antifungal, cytotoxic and SAR studies of a series of N-alkyl* N-aryl and N-alkylphenyl-I,4-pyrroledione and related compounds", Bioorganic & Medicinal Chemistry, vol. 19, No. 9, Mar. 23, 2011 (Mar. 23, 2011), pp. 2823-2834.

Selles Patrice: "Synthesis and biological evaluation of himanimide C and unnatural analogues", Organic Letters, American Chemical Society, US, vol. 7, No. 4, Feb. 17, 2005 (Feb. 17, 2005), pp. 605-608.

Benitez Sierra, et. al, International Search Report and Written Opinion dated Jul. 6, 2017, European Patent Office.

* cited by examiner

*Primary Examiner* — Alexander R Pagano
*Assistant Examiner* — Ebenezer O Sackey
(74) *Attorney, Agent, or Firm* — Florek & Endres PLLC

(57) ABSTRACT

Derivatives of pyrrole-2,5-diones having formula (I): (I) are described, together with agronomic compositions containing said derivatives having formula (I) and the use thereof for the control of phytopathogenic fungi in agricultural crops.

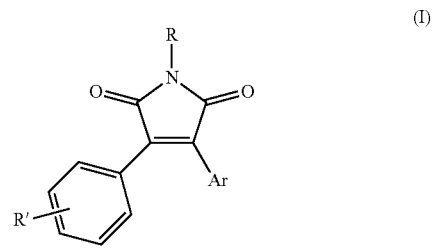

13 Claims, No Drawings

DERIVATIVES OF PYRROLE-2,5-DIONES HAVING A FUNGICIDAL ACTIVITY, THEIR AGRONOMICAL COMPOSITIONS AND USE THEREOF

The present invention relates to derivatives of pyrrole-2,5-diones having a fungicidal activity, agronomic compositions of the same and use thereof. More specifically, the present invention relates to derivatives of pyrrole-2,5-diones having formula (I)

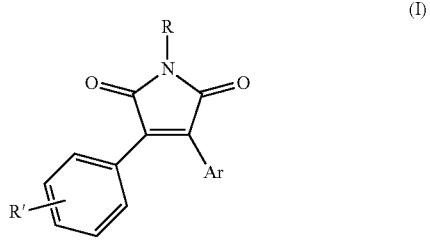

agronomic compositions containing said derivatives having formula (I) and their use for the control of phytopathogenic fungi in agricultural crops.

STATE OF THE ART

Himanimide C, corresponding to N-hydroxy-3-benzyl-4-[4-(3-methyl-2-butenyloxy)phenyl]-pyrrole-2,5-dione, is a metabolite isolated from fermentation broths of the phytopathogenic fungus *Serpula himantoides* having an antimicrobial and fungicidal activity according to what is reported in "*Zeitschrtft fuer Naturforschung, C: Journal of Biosciences*", 2002, 57 (3-4), 257-262:

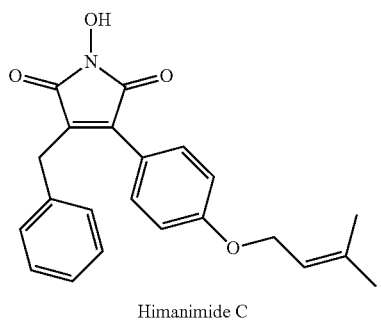 [SMILES: CC(C)=CCOc1ccc(C2=C(Cc3ccccc3)C(=O)N(O)C2=O)cc1]

Himanimide C

In Org. Lett, 2005, 7(4), 605-608, Sellès reports new synthetic routes for having access to derivatives of Himanimide C, which, however, proved to be completely inactive both in vitro and in vivo on various phytopathogenic fungi.

Other authors subsequently described the use of derivatives of pyrrole-2,5-diones as a fungicide, such as, for example, Sortino et al. in Bioorg. Med. Chem. 2011, 19, 2823-2834. This publication reports that non-substituted derivatives in positions 2 and 3 of the heterocycle have proved to be much more active than di-substituted derivatives, and specifically derivatives carrying two phenyl groups, which have proved to be completely inactive on the various strains tested.

In J. Pestic. Sci. 2012, 37(3), 247-251, Li et al. report that the polarity and steric hindrance of the substituents on the heterocycle are capable of influencing the fungicidal activity of maleic derivatives; in particular, derivatives substituted with two methyl groups in positions 2 and 3 of the heterocycle, proved to be particularly effective, even at concentrations in the order of micromoles, with respect to *Botrytis cinerea* an important phytopathogenic fungus.

A similar activity in vitro, however, has so far proved to be poorly reproducible in vivo, probably also due to a rapid metabolism of these derivatives and a low persistence in the soil, as supposed by Selles in the above-mentioned *Org. Lett.* 2005.

DESCRIPTION

The Applicant has now surprisingly found that new derivatives of pyrrole-2,5-diones carrying specific substituent groups, show a high fungicidal activity and persistency with time in vivo, allowing the practical use of these compounds for the control of phytopathogenic fungi. The object of the present invention relates to N-substituted pyrrole-2,5-diones having general formula (I):

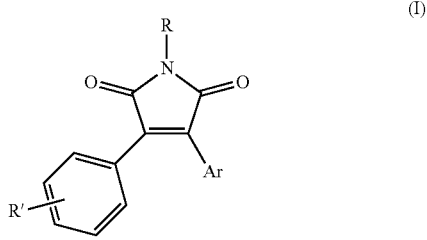

wherein:
R represents a group selected from $-OR_1$, $-NHR_2$, $-NR_3R_4$, $-SO_2R_5$ and $-Si(R_6)_3$;
Ar represents an aryl group selected from 1-naphthyl and 2-naphthyl, optionally substituted by one or more R" groups;
$R_1$ represents a group selected from a hydrogen atom, $-C(O)R_7$, $-SO_2R_8$ and $-COOR_9$;
$R_2$, $R_3$ and $R_4$ independently represent a group selected from $C_1$-$C_6$ alkyl, $C_3$-$C_6$ cycloalkyl, $C_1$-$C_6$ haloalkyl, $C_6$-$C_{12}$ alkylaryl, $-C(O)R_7$, $-SO_2R_8$ and $-COOR_9$;
$R_5$, $R_6$, $R_7$, $R_8$ and $R_9$ independently represent a group selected from $C_1$-$C_6$ alkyl, $C_3$-$C_6$ cycloalkyl, $C_1$-$C_6$ haloalkyl, $C_6$-$C_{12}$ aryl, said aryl groups being optionally substituted by one or more groups selected from $C_1$-$C_6$ alkyl or halogen atoms;
R' and R" independently represent one or more groups selected from a hydrogen atom, a halogen atom, $C_1$-$C_6$ alkyl, $C_1$-$C_6$ haloalkyl, $C_3$-$C_6$-cycloalkyl, $C_4$-$C_7$-cycloalkylalkyl, $C_1$-$C_6$-alkoxyl, $C_1$-$C_6$-haloalkoxyl, $C_1$-$C_6$-thioalkoxyl, $C_1$-$C_6$-thiohaloalkoxyl, $C_1$-$C_6$-alkylsulfinyl, $C_1$-$C_6$-alkylsulfonyl, $C_1$-$C_6$-alkoxycarbonyl, $C_3$-$C_6$-cycloalkoxycarbonyl, amino, N—$C_1$-$C_6$-alkylamino, N,N—$C_2$-$C_{12}$-dialkylamino, N—$C_1$-$C_6$ alkoxycarbonylamino, N—$C_3$-$C_6$-cycloalkylamino, N,N—$C_6$-$C_{12}$-dicycloalkylamino, N—$C_3$-$C_6$-cycloalkoxycarbonyl-amino, $C_1$-$C_6$-alkylaminocarbonyl, $C_3$-$C_6$-cycloalkylaminocarbonyl, $NR_1R_2CONR_1$—, formyl, carboxyl, cyano;
excluding compounds wherein:
R is $-OSO_2CH_3$, Ar is 1-naphthyl, R' and R" are H;
R is $-OSO_2CF_3$, Ar is 1-naphthyl, R' and R" are H;
R is $-OH$, R' is 3,4,5-OMe, Ar is 2-naphthyl, R" is H.

The above compounds are new and capable of exerting a fungicidal activity of both a curative and preventive nature, showing a low or zero phytotoxicity.

The use of N-substituted pyrrole-2,5-diones having formula (I) represents a further object of the present invention:

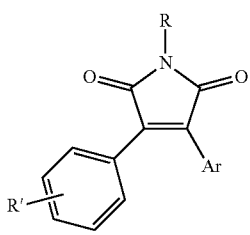

(I)

wherein:
R represents a group selected from —OR$_1$, —NHR$_2$, —NR$_3$R$_4$, —SO$_2$R$_5$ and —Si(R$_6$)$_3$;
Ar represents an aryl group selected from 1-naphthyl and 2-naphthyl, optionally substituted by one or more R" groups;
R$_1$ represents a group selected from a hydrogen atom, —C(O)R$_7$, —SO$_2$R$_8$ and —COOR$_9$;
R$_2$, R$_3$ and R$_4$ independently represent a group selected from C$_1$-C$_6$ alkyl, C$_3$-C$_6$ cycloalkyl, C$_1$-C$_6$ haloalkyl, C$_6$-C$_{12}$ alkylaryl, —C(O)R$_7$, —SO$_2$R$_8$ and —COOR$_9$;
R$_5$, R$_6$, R$_7$, R$_8$ and R$_9$ independently represent a group selected from C$_1$-C$_6$ alkyl, C$_3$-C$_6$ cycloalkyl, C$_1$-C$_6$ haloalkyl, C$_6$-C$_{12}$ aryl, said aryl groups being optionally substituted by one or more groups selected from C$_1$-C$_6$ alkyl or halogen atoms;
R' and R" independently represent one or more groups selected from a hydrogen atom, a halogen atom, C$_1$-C$_6$ alkyl, C$_1$-C$_6$ haloalkyl, C$_3$-C$_6$-cycloalkyl, C$_4$-C$_7$-cycloalkylalkyl, C$_1$-C$_6$-alkoxyl, C$_1$-C$_6$-haloalkoxyl, C$_1$-C$_6$-thioalkoxyl, C$_1$-C$_6$-thiohaloalkoxyl, C$_1$-C$_6$-alkylsulfinyl, C$_1$-C$_6$-alkylsulfonyl, C$_1$-C$_6$-alkoxycarbonyl, C$_3$-C$_6$-cycloalkoxycarbonyl, amino, N—C$_1$-C$_6$-alkylamino, N,N—C$_2$-C$_{12}$-dialkylamino, N—C$_1$-C$_6$ alkoxycarbonyl-amino, N—C$_3$-C$_6$-cycloalkylamino, N,N—C$_6$-C$_{12}$-dicycloalkylamino, N—C$_3$-C$_6$-cycloalkoxycarbonyl-amino, C$_1$-C$_6$-alkylaminocarbonyl, C$_3$-C$_6$-cycloalkylaminocarbonyl, NR$_1$R$_2$CONR$_1$—, formyl, carboxyl, cyano;
for the control of phytopathogenic fungi in agricultural crops.

Examples of halogens are: fluorine, chlorine, bromine, iodine.

Examples of linear or branched C$_1$-C$_6$ alkyls are methyl, ethyl, n-propyl, isopropyl, n-butyl, isobutyl, sec-butyl, tert-butyl, n-pentyl 3-methylbutyl, n-hexyl, 3,3-dimethylbutyl.

Examples of linear or branched C$_1$-C$_6$ haloalkyls are: fluoromethyl, difluoromethyl, trifluoromethyl, chloromethyl, dichloromethyl, 2,2,2-trifluoroethyl, 1,1,2,2-tetrafluoroethyl, pentafluoroethyl, heptafluoropropyl, 4,4,4-trichlorobutyl, 4,4-difluoropentyl, 5,5-difluorohexyl.

Examples of linear or branched C$_1$-C$_6$ alkoxyls are methoxy, ethoxy, n-propoxy, iso-propoxy, n-butoxy, isobutoxy, sec-butoxy, tert-butoxy, n-pentoxy, 3-methylbutoxy, hexyloxy, 3,3-dimethylbutoxy.

Examples of linear or branched C$_1$-C$_6$ haloalkoxyls are: fluoromethoxy, difluoromethoxy, trifluoromethoxy, chloromethoxy, dichloromethoxy, 2,2,2-trifluoroethoxy, 1,1,2,2-tetra-fluoroethoxy, 1,1,2,3,3,3-hexafluoro-propoxy, 4,4,4-trichlorobutoxy, 4,4-difluoropentoxy, 5,5-difluorohexyloxy.

Examples of C$_3$-C$_6$ cycloalkyls are cyclopropyl, cyclobutyl, cyclopentyl, cyclohexyl.

Examples of C$_3$-C$_8$ halocycloalkyls are 2,2-dichloro-cyclopropyl, 2,2-difluorocyclopropyl, 2,2,3,3-tetrafluorocyclobutyl, 3,3-difluorocyclopentyl, 2-fluorocyclohexyl.

Examples of C$_6$-C$_{12}$ alkylaryls are methyl-phenyl (benzyl), ethyl-phenyl, propyl-phenyl.

Examples of C$_6$-C$_{12}$ aryls are phenyl, naphthyl.

Examples of R' and R" groups are chlorine, bromine, fluorine, methyl, ethyl, isopropyl, trifluoromethyl, methoxy, ethoxy, trifluoromethyloxy, 1,1,2,2-tetra-fluoroethoxy.

Among the compounds having formula (I) that can be used for the control of phytopathogenic fungi in agricultural crops, compounds are preferred wherein:
R represents a group selected from —OR$_1$, —NHR$_2$, and —SO$_2$R$_5$;
Ar represents an aryl group selected from 1-naphthyl and 2-naphthyl, optionally substituted by one or more R" groups;
R$_1$ represents a group selected from a hydrogen atom, —C(O)R$_7$, —SO$_2$R$_8$ and —COOR$_9$;
R$_2$ represents a group selected from —C(O)R$_7$, —SO$_2$R$_8$ and —COOR$_9$;
R$_5$, R$_7$ and R$_8$ independently represent a group selected from C$_1$-C$_6$ alkyl, C$_3$-C$_6$ cycloalkyl, C$_1$-C$_6$ haloalkyl, C$_6$-C$_{12}$ aryl, said aryl groups being optionally substituted by one or more groups selected from C$_1$-C$_6$ alkyl or halogen atoms;
R$_9$ represents a C$_1$-C$_6$ alkyl group;
R' and R" independently represent one or more groups selected from hydrogen, halogen, C$_1$-C$_6$ haloalkyl, C$_1$-C$_6$ alkoxyl, C$_1$-C$_6$ haloalkoxyl.

Particularly preferred are compounds having formula (I) for the above-mentioned use indicated in the following Table 1

TABLE 1

| Comp. Nr. | R | R' | R" | Ar |
|---|---|---|---|---|
| 1 | OH | 2,4,6-F | H | 1-naphthyl |
| 2 | OH | 2-Br | H | 1-naphthyl |
| 3 | SO$_2$Me | H | H | 1-naphthyl |
| 4 | NH—COOEt | H | H | 1-naphthyl |
| 6 | OSO$_2$p-Tol | H | H | 1-naphthyl |
| 7 | SO$_2$—p-Tol | H | H | 1-naphthyl |
| 8 | NH—COOt-Bu | H | H | 1-naphthyl |
| 9 | OC(O)Ph | H | H | 1-naphthyl |
| 10 | NH—COOMe | H | H | 1-naphthyl |
| 11 | OC(O)Me | 2-Br | H | 1-naphthyl |
| 12 | OSO$_2$Me | 2-Br | H | 1-naphthyl |
| 13 | NH—COOEt | 2-Br | H | 1-naphthyl |
| 14 | NH—COOt-Bu | 2-Br | H | 1-naphthyl |
| 15 | OSO$_2$Me | 2,4,6-F | H | 1-naphthyl |
| 16 | OC(O)Me | 2,4,6-F | H | 2-naphthyl |
| 17 | OH | 2-Br | 4-F | 1-naphthyl |
| 18 | OH | 2-Br | 6-OMe | 2-naphthyl |

As already indicated, the compounds having formula (I) have a high fungicidal activity and persistence in the soil and they do not show any phytotoxicity with respect to the crops to which they are applied. These characteristics make them suitable for use in the agricultural field for defense against phytopathogenic fungi.

Examples of fungi that can be effectively fought with the compounds having formula (I) according to the present invention belong to the classes of Basidiomycetes, Ascomycetes, Deuteromycetes or imperfect fungi, Oomycetes: Puccinia spp., *Ustilago* spp., *Tilletia* spp., *Uromyces* spp., *Phakopsora* spp., *Rhizoctonia* spp., *Erysiphe* spp., *Sphaerotheca* spp., *Podosphaera* spp., *Uncinula* spp., *Helminthosporium* spp., *Rhynchosporium* spp., *Pyrenophora* spp., *Monilinia* spp., *Sclerotinia* spp., *Septoria* spp. (*Mycosphaerella* spp.), *Venturia* spp., *Botrytis* spp., *Alternaria* spp., *Fusarium* spp., *Cercospora* spp., *Cercosporella herpotrichoides, Colletotrichum* spp., *Pyricularia oryzae, Sclerotium* spp., *Phytophthora* spp., *Pythium* spp., *Plasmopara viticola, Peronospora* spp., *Pseudoperonospora cubensis, Bremia lactucae.*

The main crops that can be protected with the compounds having formula (I) according to the present invention comprise cereals (wheat, barley, rye, oats, rice, corn, sorghum etc.), fruit-trees (apples, pears, plums, peaches, almonds, cherries, bananas, grapes, strawberries, raspberries, blackberries, etc.), citrus fruit (oranges, lemons, mandarins, grapefruit, etc.), legumes (beans, peas, lentils, soybeans, etc.), vegetables (spinach, lettuce, asparagus, cabbages, carrots, onions, tomatoes, potatoes, eggplants, peppers, etc.), cucurbits (pumpkins, zucchini, cucumbers, melons, watermelons, etc.), oil plants (sunflower, rapeseed, peanut, castor, coconut, etc.), tobacco, coffee, tea, cocoa, sugar beet, sugar cane, cotton.

The processes for the preparation of pyrrole-2,5-diones having formula (I) are described hereunder.

As is well known to skilled persons in the field, the pyrrole-2,5-diones having formula (I) can be prepared in a few synthesis steps starting from the corresponding maleic anhydride having formula (II) as indicated in scheme 1

Scheme 1

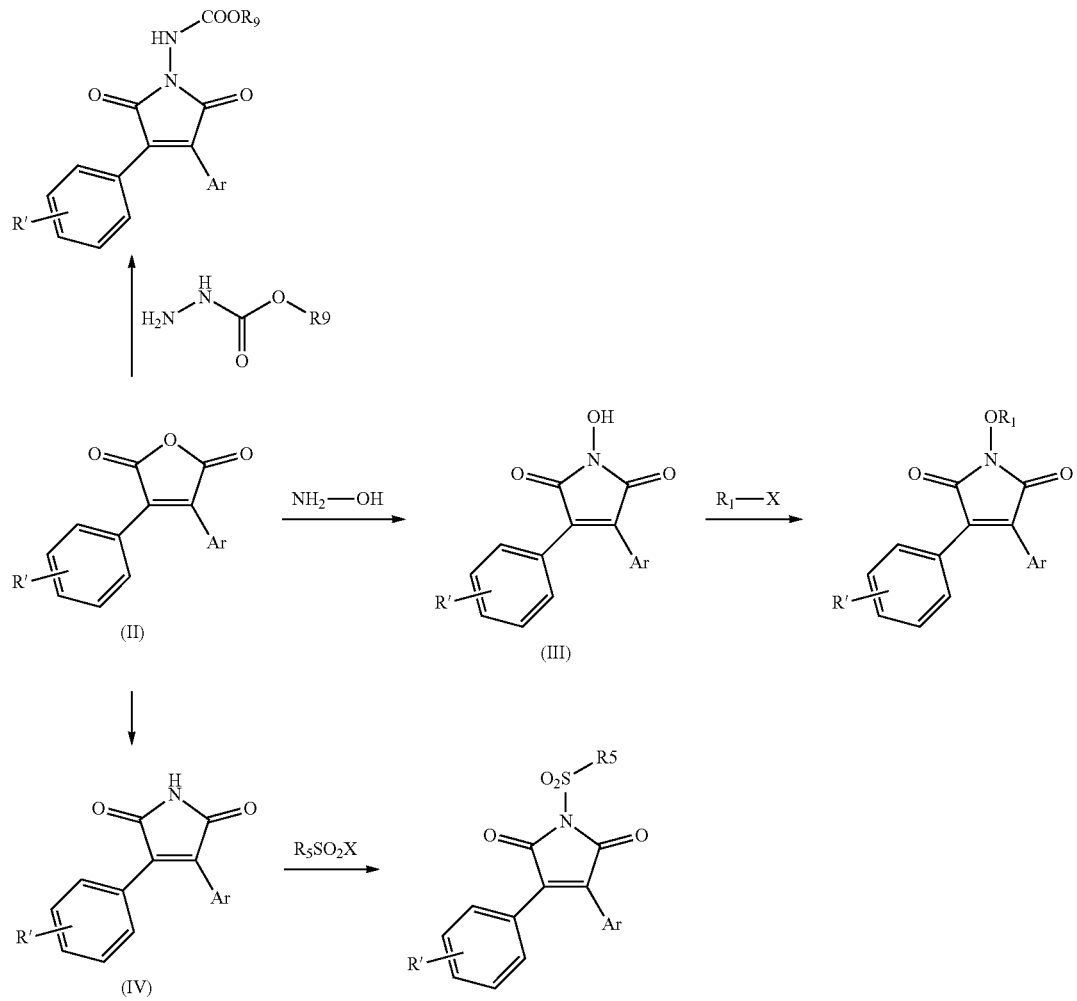

wherein X is a leaving group and R', Ar, $R_1$, $R_5$ and $R_9$ are as defined above.

According to a first aspect, when R represents an —$OR_1$ group, wherein $R_1$ has the above meaning, the maleic anhydride having formula (II) is reacted with hydroxylamine or one of its salts, possibly in the presence of a suitable solvent; amides such as N,N-dimethylformamide or N-methyl-pyrrolidone, or amines such as pyridine can be used as solvent.

Said hydroxylamine, or one of its salts, is preferably added in a molar ratio ranging from 1 to 3, more preferably in a molar ratio equal to about 2, with respect to the quantity of maleic anhydride having formula (II).

The reaction is carried out at a temperature ranging from 50 to 200° C., preferably at the reflux temperature of the solvent used.

When the group $R_1$ in the compound having formula (I) is different from hydrogen, the hydroxyl group of the N-hydroxyimide having formula (III) thus obtained is subsequently subjected to substitution by the addition of an alkylating agent having formula $R_1$—X wherein X is a leaving group. Said reaction envisages the use of a base, preferably an organic base, more preferably selected from triethylamine, diisopropylethylamine, pyridine.

The above substitution reaction is preferably carried out in a solvent, more preferably in a solvent selected from ethers such as ethyl ether, tetrahydrofuran, dioxane, chlorinated solvents such as dichloromethane, chloroform, dichloroethane and esters such as vinyl acetate.

According to a further aspect, when R represents a —$NHR_2$ group, wherein $R_2$ is preferably a —$COOR_9$ group and $R_9$ has the above meaning, the compound having formula (I) is prepared in a single synthesis step by adding a carbazate having formula $NH_2$—NH—$COOR_9$ in a molar ratio ranging from 0.5 to 2, preferably in a molar ratio equal to about 1 with respect to the quantity of maleic anhydride having formula (II).

Said reaction envisages the use of a suitable solvent and is carried out at a temperature ranging from 50 to 200° C., preferably at the reflux temperature of the solvent.

Examples of suitable solvents are aromatic hydrocarbons, such as benzene or toluene.

According to a further aspect, when R represents —$SO_2R_5$ wherein $R_5$ has the above meaning, the maleic anhydride having formula (II) is converted into the corresponding imide having formula (IV), by carrying out the reaction in formamide at a temperature ranging from 80 to 220° C., preferably at about 120° C.

The imide having formula (IV) thus obtained is subsequently subjected to a substitution reaction with an alkylating agent having formula $R_5SO_2$—X wherein $R_5$ has the above meaning and X is a leaving group.

Said reaction envisages the use of a base, preferably an organic base, more preferably selected from triethylamine, diisopropylethylamine, pyridine.

The above substitution reaction is preferably carried out in a solvent, more preferably in a solvent selected from ethers such as ethyl ether, tetrahydrofuran, dioxane, chlorinated solvents such as dichloromethane, chloroform, dichloroethane and esters such as ethyl acetate at a temperature ranging from room temperature to the reflux temperature of the solvent selected, preferably at about 50° C.

The maleic hydride having formula (II), which is a key intermediate for the preparation of compounds having formula (I), when not available on the market, can be easily obtained according to methods known in the art, as described, for example, in J. Heter. Chem. 2011, 48, 1243-1250 or in J. Org. Chem. 1990, 55, 5165-5170.

For practical uses in agriculture, it is often preferable to use the compounds of the present invention suitably formulated in agronomic compositions comprising one or more compounds having formula (I) and agronomically acceptable co-formulants.

A further object of the present invention therefore relates to fungicidal agronomic compositions comprising one or more compounds having formula (I), a solvent and/or solid, liquid or liquefied diluent, possibly one or more surfactant(s) and other agronomically acceptable co-formulants.

Compositions can be used in the form of dry powders, wettable powders, emulsifiable concentrates, micro-emulsions, pastes, granulates, solutions, suspensions, fumigants, etc.: the selection of the type of composition depends on the specific use.

The compositions are prepared according to known methods, for example by diluting or dissolving the active substance with a solvent medium and/or solid diluent, possibly in the presence of surfactants.

Kaolin, alumina, silica, talc, bentonite, gypsum, quartz, dolomite, attapulgite, montmorillonite, diatomaceous earth, cellulose, starch, etc., can be used as solid inert diluents, or carriers.

Inert liquid diluents that can be used are water, or organic solvents such as aromatic hydrocarbons (xylols, blends of alkyl benzenes, etc.), aliphatic hydrocarbons (hexane, cyclohexane, etc.) halogenated aromatic hydrocarbons (chlorobenzene, etc.), alcohols (methanol, propanol, butanol, octanol, etc.), esters (isobutyl acetate, etc.), ketones (acetone, cyclohexanone, acetophenone, isophorone, ethylamylketone etc.), or vegetable or mineral oils or mixtures thereof, etc.

Propellant gases such as butane, propane, halogenated hydrocarbons, nitrogen or carbon dioxide can be used as liquefied diluents or liquefied substances that gasify at room temperature and atmospheric pressure.

Surfactants that can be used are wetting and emulsifying agents of the non-ionic type (polyethoxylated alkyl phenols, polyethoxylated fatty alcohols, etc.), of the anionic type (alkylbenzenesulfonates, alkylsulfonates, etc.), of the cationic type (alkyl ammonium quaternary salts, etc.).

Dispersing agents can also be added (for example lignin and its salts, cellulose derivatives, alginates, etc.), stabilizers (for example antioxidants, UV absorbers, etc.).

The concentration of active compound having formula (I) in the above compositions can vary within a wide range and depends on various factors. It varies in relation to the active compound having formula (I), the applications for which said compositions are destined, the environmental conditions and the type of formulation adopted. The concentration of active compound having formula (I) generally ranges from 0.1 to 90% by weight with respect to the total weight of the composition, preferably from 0.5 to 90% by weight.

The compounds of the present invention as such or formulated can be used in a mixture with other active ingredients such as, for example, insecticides, acaricides, nematocides, herbicides, fungicides other than those having formula (I), bactericides, fertilizers and biostimulants, etc. for broadening their range or preventing resistance.

In some cases, the mixtures thus obtained have a synergic effect between the components, which causes the mixture, for example, to exert a higher activity with respect to that of the single elements of which it is composed.

Examples of insecticides, acaricides, nematocides that can be added to the compositions containing one or more compounds having general formula (I) are the following: abamectin, acetamiprid, acrinathrin, alphacypermethrin, alphamethrin, azadirachtin, *Bacillus subtilis, Bacillus thuringiensis, Beauveria bassiana*, betacyfluthrin, bifenazate, bifenthrin, buprofezin, chlorpyrifos, chlorpyrifos M, clofentezine, cyhalothrin, cyhexatin, cypermethrin, cyromazine, chloropicrin, clorantranilipide, clotianidin, deltamethrin, diflubenzuron, dimethoat, dazonet, sulfuryl difluoride, dimethyldisulfide, emamectin, esfenvalerate, ethoprophos, etofenprox, etoxazole, fenamiphos, fenazaquin, fenoxycarb, fenpyroximate, fipronil, fluazinam, flufenoxuron, fluvalinate, fosthiazate, formentanate, flonicamid, formet, viruses, hexythiazox, imidaclopridi, indoxacarb, lambda-cyhalothrin, lufenuron malathion, metaldehyde, methamidophos, *Metharhizium* spp, methiocarb, methomyl, methoxyfenozide, milbemectin, metaflumizone, metam sodium, metam potassium, oxamyl, *Paecilomyces fumosoroseus*, phosmet, pirimicarb, pirimiphos M, pyrethrum, pyridaben, pyriproxyfen, piperonyl butoxide, spinosad, spironesifen, spirotetramat, spinetoran, spirodiclofen, tau-fluvalinate, tebufenozide, tebufenpyrad, teflubenzuron, tefluthrin, thiacloprid, triflumuron, zeta-cypermethrin, (1R-cis)-[5-(phenylmethyl)-3-furanyl]-methyl-3-[(dihydro-2-oxo-3(2H)-furanylidene) methyl]-2,2-dimethyl-cyclo-propanecarboxylate, (3-phenoxyphenyl)-methyl-2,2,3,3-tetramethyl-cyclopropanecarboxylate, 1-[(2-chloro-5-thiazolyl)methyl]-5-triazine 2-(1H)-imine, 2-(2-chloro-6-fluorophenyl)-4-[4-(1,1-dimethylethyl)-phenyl]-4,5-dihydro-oxazol, 2-(acetyloxy)-3-dodecyl-1,4-naph-thalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl-propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thiol]-3-(2H)-pyridazinone, 4-chloro-2-(2-chloro-2-methylpropyl)-5-[(6-iodo-3-pyridinyl)(2-chloro-2-methylpropyl)-5-[(6-iodo-3-pyridinyl)-methoxy]-3-(2H)pyridazinone, 4-chloro-5-[(6-chloro-3-pyridinyl)methoxy]-2-(3,4-di-chlorophenyl)-3 (2H)pyridazinone, *Bacillus thuringiensis* strain EG-2348, [2-benzoyl-1-(1,1-dimethylethyl)-hydrazine] benzoic acid, 2,2-dimethyl-3-(2,4-dichlorophenyl)-2-oxo-1-oxaspiro [4.5]-dec-3-en-4-yl butanoate, [3-[(6-chloro-3-pyridinyl)-methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyrid-azinyl] oxy]ethyl]-carbamate, N-(3,4,4-trifluoro-1-oxo-3-butenyl)-glycine, N-(4-chlorophenyl)-3-[4-(difluoro-methoxy)-phenyl]-4,5-dihydro-4-phenyl-1H-pyrazole-1-carboxamide, N-[(2-chloro-5-thiazolyl)-methyl]-N'-methyl-N"-nitro-guanidine, N-methyl-N'-(1-methyl-2-propenyl)-1,2-hydrazinedicarbo-thioamide, N-methyl-N'-2-propenyl-1,2-hydrazinedicarbo-thioamide, O,O-diethyl[2-(dipropylamino)-2-oxoethyl]-ethyl-phosphoro-amidothioate.

Examples of herbicides that can be added to the compositions containing one or more compounds having general formula (I) are the following: acetochlor, acifluorfen, aclonifen, AKH-7088 ({methyl (E,Z)-[[[1-[2-chloro-4-(trifluoromethyl)phenoxy]-2-nitrophenyl]-2-methoxyethylidene] amino]acetate}), alachlor, alloxydim, ametryn, amicarbazone, amidosulfuron, amitrole, anilofos, asulam, atrazine, azafenidin, azimsulfuron, aziprotryne, BAY MKH 6561 (methyl 2-({[(4-methyl-5-oxo-3-propoxy-4,5-dihydro-1H-1,2,4-triazol-1-yl)carbonyl] amino}sulfonyl)benzoate sodium salt), beflubutamid, benazolin, benfluralin, benfuresate, bensulfuron, bensulide, bentazone, benzfendizone, benzobicyclon, benzofenap, benzthiazuron, bifenox, bilanafos, bispyribac-sodium, bromacil, bromobutide, bromofenoxim, bromoxynil, butachlor, butafenacil, butamifos, butenachlor, butralin, butroxydim, butylate, cafenstrole, carbetamide, carfentrazone-ethyl, chlomethoxyfen, chloramben, chlorbromuron, chlorbufam, chlorflurenol, chloridazon, chlorimuron, chlornitrofen, chlorotoluron, chloroxuron, chlorpropham, chlorsulfuron, chlorthal, chlorthiamid, cinidon ethyl, cinmethylin, cinosulfuron, clethodim, clodinafop, clomazone, clomeprop, clopyralid, cloransulam-methyl, cumyluron (JC-940), cyanazine, cycloate, cyclosulfamuron, cycloxydim, cyhalofop-butyl, 2,4-D, 2,4-DB, daimuron, dalapon, desmedipham, desmetryn, dicamba, dichlobenil, dichlorprop, dichlorprop-P, diclofop, diclosulam, diethatyl, difenoxuron, difenzoquat, diflufenican, diflufenzopyr, dimefuron, dimepiperate, dimethachlor, dimethametryn, dimethenamid, dinitramine, dinoseb, dinoseb acetate, dinoterb, diphenamid, dipropetryn, diquat, dithiopyr, 1-diuron, eglinazine, endothal, EPTC, esprocarb, ethalfluralin, ethametsulfuron-methyl, ethidimuron, ethiozin (SMY 1500), etho- fumesate, ethoxyfen-ethyl (HC-252), ethoxysulfuron, etobenzanid (HW 52), fenoxaprop, fenoxaprop-P, fentrazamide, fenuron, flamprop, flamprop-M, flazasulfuron, florasulam, fluazifop, fluazifop-P, fluazolate (JV 485), flucarbazone-sodium, fluchloralin, flufenacet, flufenpyr ethyl, flumetsulam, flumiclorac-pentyl, flumioxazin, flumipropin, fluometuron, fluoroglycofen, fluoronitrofen, flupoxam, flupropanate, flupyrsulfuron, flurenol, fluridone, flurochloridone, fluroxypyr, flurtamone, fluthiacet-methyl, fomesafen, foramsulfuron, fosamine, furyloxyfen, glufosinate, glyphosate, halosulfuron-methyl, haloxyfop, haloxyfop-P-methyl, hexazinone, imazamethabenz, imazamox, imazapic, imazapyr, imazaquin, imazethapyr, imazosulfuron, indanofan, iodosulfuron, ioxynil, isopropalin, isoproturon, isouron, isoxaben, isoxachlortole, isoxaflutole, isoxapyrifop, KPP-421, lactofen, lenacil, linuron, LS830556 [[[2-methyl(methylsulfonyl)amino]-2-oxoethyl]amino]methylphosphonic acid, MCPA 2-methyl-4-chlorophenoxyacetic acid, MCPA-thioethyl, MCPB (4-(4-chloro-2-methylphenoxy)butanoic acid), mecoprop, mecoprop-P, mefenacet, mesosulfuron, mesotrione, metamitron, metazachlor, methabenzthiazuron, methazole, methoprotryne, methyldymron, metobenzuron, metobromuron, metolachlor, S-metolachlor, metosulam, metoxuron, metribuzin, metsulfuron, molinate, monalide, monolinuron, naproanilide, napropamide, naptalam, NC-330 (methyl 5-[(4,6-dimethylpyrimidin-2-yl)carbamoylsulfamoyl]1-pyridin-2-yl pyrazol-4-carboxylate), neburon, nicosulfuron, nipyraclofen, norflurazon, orbencarb, oryzalin, oxadiargyl, oxadiazon, oxasulfuron, oxaziclomefone, oxyfluorfen, paraquat, pebulate, pendimethalin, penoxsulam, pentanochlor, pentoxazone, pethoxamid, phenmedipham, picloram, picolinafen, piperophos, pretilachlor, primisulfuron, prodiamine, profluazol, proglinazine, prometon, prometryne, propachlor, propanyl, propaquizafop, propazine, propham, propisochlor, propyzamide, prosulfocarb, prosulfuron, pyraclonil, pyraflufen-ethyl, pyrazogyl (HSA-961), pyrazolynate, pyrazosulfuron, pyrazoxyfen, pyribenzoxim, pyributicarb, pyridafol, pyridate, pyriftalid, pyriminobac-methyl, pyrithiobac-sodium, pyroxasulfone quinclorac, quinmerac, quizalofop, quizalofop-P, rimsulfuron, sethoxydim, siduron, simazine, simetryn, sulcotrione, sulfentrazone, sulfometuron-methyl, sulfosulfuron, 2,3,6-TBA, TCA-sodium, tebutam, tebuthiuron, tepraloxydim, terbacil, terbumeton, terbuthyl-azine, terbutryn, thenylchlor, thiazafluron, thiazopyr, thidiazimin, thifensulfuron-methyl, thiobencarb, tiocarbazil, tioclorim, tralkoxydim, tri-allate, triasulfuron, triaziflam, tribenuron, triclopyr, trietazine, trifloxysulfuron, trifluralin, triflusulfuron-methyl, tritosulfuron, UBI-C4874 (quizalofop-P), vernolate.

Examples of fungicides that can be added to the compositions containing one or more compounds having general formula (I) are the following: acibenzolar, ametoctradin, amisulbrom, ampropylfos, anilazine, azaconazole, azoxystrobin, benalaxyl, benalaxyl-M, benomyl, benthiavalicarb, bitertanol, bixafen, blasticidin-S, boscalid, bromuconazole, bupirimate, buthiobate, captafol, captan, carbendazim, carboxin, carpropamid, chinomethionat, chloroneb, chlorothalonil, chlozolinate, cyazofamid, cyflufenamid, cymoxanil, cyproconazole, cyprodinil, debacarb, dichlofluanid, dichlone, diclobutrazol, diclomezine, dicloran, diclocymet, diethofencarb, difenoconazole, diflumetorim, dimethirimol, dimethomorph, dimoxystrobin, diniconazole, dinocap, dipyrithione, ditalimfos, dithianon, dodemorph, dodine, edifenphos, epoxiconazole, etaconazole, ethaboxam, ethirimol, ethoxyquin, etridiazole, famoxadone, fenamidone, fenaminosulf, fenapanil, fenarimol, fenbuconazole, fenfuram, fenhexamid, fenoxanil, fenpiclonil, fenpropidin, fenpropimorph, fenpyrazamine, fentin, ferbam, ferimzone, fluazinam, fludioxonil, fluindapyr ((RS)-3-(difluoromethyl)-N-(7-fluoro-2,3-dihydro-1,1,3-trimethyl-1H-inden-4-yl)-1-methyl-1H-pyrazole-4-carboxamide), flumetover, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, fosetyl-aluminium, fuberidazole, furalaxyl, furametpyr, furconazole, furconazole-cis, guazatine, hexaconazole, hymexazol, hydroxyquinoline sulfate, imazalil, imibenconazole, iminoctadine, ipconazole, iprobenfos, iprodione, isoprothiolane, iprovalicarb, isopyrazam, isotianil, kasugamycin, kresoxim-methyl, mancopper, mancozeb, mandipropamid, maneb, mebenil, mepanipyrim, mepronil, meptyldinocap, metalaxyl, metalaxyl-M, metconazole, methfuroxam, metiram, metominostrobin, metrafenone, metsulfovax, myclobutanil, natamycin, nicobifen, nitrothal-isopropyl, nuarimol, ofurace, orysastrobin, oxadixyl, oxpoconazole, oxycarboxin, pefurazoate, penconazole, pencycuron, penflufen, pentachlorofenol and its salts, penthiopyrad, phthalide, picoxystrobin, piperalin, Bordeaux mixture, polyoxins, probenazole, prochloraz, procymidone, propamocarb, propiconazole, propineb, proquinazid, prothiocarb, prothioconazole, pyracarbolid, pyraclostrobin, pyrametostrobin, pyraoxystrobin, pyrazophos, pyribencarb, pyrifenox, pyrimethanil, pyriofenone, pyroquilon, pyroxyfur, quinacetol, quinazamid, quinconazole, quinoxyfen, quintozene, rabenzazole, copper hydroxide, copper oxychloride, copper (I) oxide, copper sulfate, sedaxane, silthiofam, simeconazole, spiroxamine, streptomycin, tebuconazole, tebufloquin, tetraconazole, thiabendazole, thiadifluor, thicyofen, thifluzamide, thiophanate, thiophanate-methyl, thiram, tiadinil, tioxymid, tolclofos-methyl, tolylfluanid, triadimefon, triadimenol, triarimol, triazbutil, triazoxide, tricyclazole, tridemorf, trifloxystrobin, triflumizole, triforine, triticonazole, uniconazole, uniconazole-P, validamycin, valifenalate, vinclozolin, zineb, ziram, sulfur, zoxamide.

Examples of bactericides that can be added to the compositions containing one or more compounds having general formula (I) are the following: bronopol, dichlorophen, nitrapyrina, nickel dimethyldithiocarbamate, kasugamycin, octhilinone, furancarboxylic acid, probenazole, streptomycin, tecloftalam, copper hydroxide, copper oxychloride, copper (I) oxide, copper sulfate, copper salicylate.

Examples of fertilizers and biostimulants that can be added to the compositions containing one or more compounds having general formula (I) are the following: mixtures of amino acids and/or oligopeptides of an animal and/or vegetable origin, 4-thiazolidinecarboxylic acid, 4-acetylthiazolidine-carboxylic acid, ectoin, phytosterols.

A further object of the present invention therefore relates to agronomic compositions comprising at least one compound having formula (I) and at least a second active ingredient selected from insecticides, acaricides, nematocides, herbicides, fungicides other than those having formula (I), bactericides, fertilizers and biostimulants.

The compositions object of the present invention are capable of exerting a fungicidal action that can be of a curative and/or preventive nature and generally have an extremely low or zero phytotoxicity with respect to the crops treated.

A further object of the present invention therefore relates to the use of compositions comprising at least one compound having formula (I) for the control of phytopathogenic fungi.

When the compositions comprise a compound having formula (I) and at least a further known active principle, the weight ratios in the above compositions, between the compound having formula (I) and the further known active principles, range according to the compounds selected and can normally be within the range of 1:100 to 100:1, preferably from 1:10 to 10:1.

The total concentration of active components in the above compositions can vary within a wide range; they generally range from 1% to 99% by weight with respect to the total weight of the composition, preferably from 5 to 90% by weight with respect to the total weight of the composition.

The compounds having formula (I) or the compositions containing them can be applied to the crop via the leaves, or to the soil by means of fertigation, or incorporation into the ground, or through seed tanning.

A further object of the present invention therefore relates a method for the control of phytopathogenic fungi in agricultural crops, which consists in applying effective and non-phytotoxic doses of compositions of compounds having formula (I) used as such or formulated in fungicidal compositions as described above.

The quantity of compound to be applied for obtaining the desired effect can vary in relation to various factors such as, for example, the compound used, the crop to be protected, the degree of infestation, the climatic conditions, the characteristics of the soil, the method of application, etc.

Doses of compound having formula (I) ranging from 100 g to 10,000 g per hectare of agricultural crop or, in the case of compositions comprising other known active principles, overall doses of active principles ranging from 100 g to 20,000 g per hectare of agricultural crop generally provide a sufficient control.

Doses of compound having formula (I) ranging from 500 g to 800 g per hectare of agricultural crop are preferably used.

The following illustrative and non-limiting examples are provided for a better understanding of the invention.

EXPERIMENTAL PART

Example 1

Preparation of 3-(2-bromophenyl)-1-(methane-sulfonyloxy)-4-(1-naphthyl)-1H-pyrrole-2,5-dione [Compound Nr. 12]

a) Preparation of 2-bromophenylglyoxylic Acid 8.3 g (75 mmoles) of selenium dioxide were added to 10 g (50 mmoles) of 2'-bromoacetophenone dissolved in 20 ml of pyridine; the mixture was left under magnetic stirring at 100° C. for 2 hours.

After control in TLC and LC-MS, the mixture was filtered to eliminate the selenium and the pyridine was removed at reduced pressure. The residue was acidified with diluted HCl and extracted with ethyl acetate; the phases were then separated; the aqueous phase was re-extracted twice with ethyl acetate. The organic phases were joined and washed with water and a saturated solution of NaCl.

After anhydrification on sodium sulfate, filtration and evaporation of the solvent at reduced pressure, 11.4 g of the desired product (50 mmoles) were obtained, as a cream-coloured solid. The raw product thus obtained was used for the subsequent reaction. Quantitative yield.

LC-MS [M+H]=229.

b) Preparation of 3-(2-bromophenyl)-4-(1-naphthyl)-furan-2,5-dione [Anhydride Having Formula Generale (II)]

A suspension under nitrogen of 5.0 g (24.0 mmoles) of sodium 1-naphthylacetate and 5.5 g (24.0 mmoles) of 2-bromophenylglyoxylic acid in 36 ml acetic anhydride was heated under stirring to reflux temperature for 2 hours.

The reaction trend was controlled in TLC and GC-MS. The acetic anhydride was removed at reduced pressure, water and ethyl acetate were added to the mixture, and the phases then were separated; the aqueous phase was re-extracted twice with ethyl acetate. The organic phases were joined and washed with water and a saturated solution of sodium chloride.

After anhydrification on sodium sulfate, filtration and evaporation of the solvent at reduced pressure, 8.6 g of the desired product (22.8 mmoles) were obtained, as a yellow solid. Yield 95%

LC-MS [M+H]=379 c) Preparation of 3-(2-bromophenyl)-1-hydroxy-4-(1-naphthyl)-1H-pyrrole-2,5-dione [N-hydroxyimide Having General Formula (III)]

3.17 g (45.6 mmoles) of hydroxylamine hydrochloride were added to a suspension of 8.6 g (22.8 mmoles) of 3-(2-bromophenyl)-4-(1-naphthyl)furan-2,5-dione in 60 ml of pyridine anhydrified on sieves. The mixture was left under stirring at reflux temperature for 2 hours. After control in TLC and LC-MS, the solvent was removed at reduced pressure, water and ethyl acetate were added to the mixture, and the phases were then separated; the aqueous phase was re-extracted twice with ethyl acetate. The organic phases were joined and washed with water and a saturated solution of sodium chloride.

After anhydrification on sodium sulfate, filtration and evaporation of the solvent at reduced pressure, 11 g of yellow solid were obtained. The raw product was purified on a heptane:ethyl acetate 7:3 column, obtaining 7.6 g (19.4 mmoles) of the desired product as a yellow solid. Yield 85%

LC-MS [M+H]=394 d) Preparation of 3-(2-bromophenyl)-1-methanesulfonyl-oxy-4-(1-naphthyl)-1H-pyrrole-2,5-dione [Compound Having General Formula (I)]

2.98 ml (21.4 mmoles) of triethylamine were added to a suspension of 7.6 g (19.4 mmoles) of 3-(2-bromophenyl)-1-hydroxy-4-(1-naphthyl)-1H-pyrrole-2,5-dione in 40 ml of dichloromethane, and 1.66 ml (21.4 mmoles) of mesyl chloride diluted in 10 ml of dichloromethane were subsequently added dropwise on an ice bath. The mixture was left under stirring at room temperature for 2 hours.

After control in TLC and LC-MS, water and ethyl acetate were added to the mixture, and the phases were then separated; the aqueous phase was re-extracted twice with dichloromethane. The organic phases were joined and washed with water and a saturated solution of sodium chloride.

After anhydrification on sodium sulfate, filtration and evaporation of the solvent at reduced pressure, 12 g of an orange oil were obtained, which tends to solidify. The raw product thus obtained was purified on a chromatographic column (SiO$_2$ heptane:ethyl acetate 8:2), obtaining 8.1 g (17.1 mmoles) of the desired product as a yellow solid. Yield 88%

LC-MS [M+H]=473

Example 2

Preparation of ethyl 3-(2-bromophenyl)-4-(1-naphthyl)-2,5-dione-1H-pyrrolylcarbamate [Compound Nr. 13]

41 g (39.6 mmoles) of ethyl carbazate were added to a suspension of 15 g (39.6 mmoles) of 3-(2-bromophenyl)-4-(1-naphthyl)furan-2,5-dione, obtained as in Example 1 b), in 150 ml of anhydrous toluene. The mixture was left under stirring at reflux temperature for 2 hours in a flask equipped with a Dean-Stark for extraction of the reaction water.

After control in TLC and LC-MS, the solvent was evaporated at reduced pressure and 18.5 g of a solid were obtained, which was purified on a chromatographic column (SiO$_2$ heptane:ethyl acetate 8:2), obtaining 17 g (36.6 mmoles) of the desired product as a cream-coloured solid. Yield 92%

LC-MS [M+H]=465

Example 3

Preparation of t-butyl 3-phenyl-4-(1-naphthyl)-2,5-dione-1H-pyrrolylcarbamate [Compound Nr. 8]

66.5 g (50 mmoles) of t-butyl carbazate were added to a suspension of 15 g (50 mmoles) of 3-phenyl-4-(1-naphthyl)-furan-2,5-dione, obtained as in Example 1 b), in 150 ml of anhydrous toluene. The mixture was left under stirring at reflux temperature for 2 hours in a flask equipped with a Dean-Stark for extraction of the reaction water.

After control in TLC and LC-MS, the solvent was evaporated at reduced pressure and 22 g of a solid were obtained, which was purified on a chromatographic column (SiO$_2$ heptane:ethyl acetate 8:2), obtaining 19 g (46 mmoles) of the desired product as a yellow solid. Yield 92%

LC-MS [M+H]=414

Example 4

Preparation of 1-methanesulfonyl-3-phenyl-4-(1-naphthyl)-1H-pyrrol-2,5-dione [Compound Nr. 3]

a) Preparazione di 3-phenyl-4-(1-naphthyl)-1H-pyrrole-2,5-dione [mide Having General Formula (IV)]

4.0 g (13.3 mmoles) of 3-phenyl-4-(1-naphthyl)furan-2,5-dione, obtained as described in Example 1 b), were dissolved in 10 ml of formamide and the mixture was left under stirring at a temperature of 120° C. for 8 hours in a test-tube closed with a Teflon stopper.

After control in TLC and LC-MS, water and ethyl acetate were added to the mixture, and the phases were then separated; the aqueous phase was re-extracted twice with ethyl acetate. The organic phases were joined and washed with water and a saturated solution of sodium chloride.

After anhydrification on sodium sulfate, filtration and evaporation of the solvent at reduced pressure, 4.3 g of a yellow oil were obtained, which tends to solidify. The raw product thus obtained was ground with a mixture of ethyl ether and heptane, filtered and dried in air, obtaining 3.08 g (10.3 mmoles) of the desired product as a yellow solid. Yield 77%

LC-MS [M+H]=299 b) Preparation of 3-phenyl-1-methanesulfonyl-4-(1-naphthyl)-1H-pyrrole-2,5-dione [Compound Having General Formula (I)]

4.2 ml (30 mmoles) of triethylamine were added to a solution of 3.0 g (10 mmoles) of 3-phenyl-4-(1-naphthyl)-1H-pyrrol-2,5-dione in 15 ml of anhydrous dimethylformamide and 2.33 ml (30 mmoles) of mesyl chloride were subsequently added dropwise on an ice bath. The mixture was left under stirring at 50° C. in a closed tube for 8 hours.

After control in TLC and LC-MS, water and ethyl acetate were added to the mixture, and the phases were then separated; the aqueous phase was re-extracted twice with ethyl acetate. The organic phases were joined and washed with water and a saturated solution of sodium chloride.

After anhydrification on sodium sulfate, filtration and evaporation of the solvent at reduced pressure, 5 g of an orange oil were obtained, which tends to solidify. The raw product thus obtained was purified on a chromatographic column ($SiO_2$ heptane:ethyl acetate 8:2), obtaining 2 g (5.3 mmoles) of the desired product as a yellow solid. Yield 53%

LC-MS [M+H]=377

Example 5

Preparation of 1-(methanesulfonyloxy)-3-(2,4,6-trifluorophenyl)-4-(1-naphthyl)-1H-pyrrole-2,5-dione [Composto Nr. 15]

a) Preparation of 2,4,6-trifluorophenylglyoxylic Acid 9.6 g (86.2 mmoles) of selenium dioxide were added to 10 g (57.4 mmoles) of 2,4,6-trifluoroacetophenone dissolved in 20 ml of pyridine; the mixture was left under magnetic stirring at 100° C. for 2 hours.

After control in TLC and LC-MS, the mixture was filtered to eliminate the selenium and the pyridine was removed at reduced pressure. The residue was acidified with diluted HCl and extracted with ethyl acetate; the phases were then separated; the aqueous phase was re-extracted twice with ethyl acetate. The organic phases were joined and washed with water and a saturated solution of NaCl.

After anhydrification on sodium sulfate, filtration and evaporation of the solvent at reduced pressure, 11.0 g of the desired product (50 mmoles) were obtained as a cream-coloured solid. The raw product thus obtained was used for the subsequent reaction. Quantitative yield.

LC-MS [M+H]=204 b) Preparation of 3-(2,4,6-trifluorophenyl)-4-(1-naph-thyl)furan-2,5-dione [Anhydride Having General Formula (II)]

A suspension under nitrogen of 5.0 g (24.0 mmoles) of sodium 1-naphthylacetate and 4.9 g (24.0 mmoles) of 2,4,6-trifluorophenylglyoxylic acid in 36 ml of acetic anhydride was heated under stirring to reflux temperature for 2 hours.

The reaction trend was controlled in TLC and in GC-MS. The acetic anhydride was removed at reduced pressure, water and ethyl acetate were added to the mixture, and the phases were then separated; the aqueous phase was re-extracted twice with ethyl acetate. The organic phases were joined and washed with water and a saturated solution of sodium chloride.

After anhydrification on sodium sulfate, filtration and evaporation of the solvent at reduced pressure, 8.15 g of the desired product (23.0 mmoles) were obtained, as a yellow solid. Yield 96%

LC-MS [M+H]=354 c) Preparation of 1-hydroxy-3-(2,4,6-trifluorophenyl)-4-(1-naphthyl)-1H-pyrrole-2,5-dione [N-hydroxyimide Having General Formula (III)]

3.20 g (46 mmoles) of hydroxylamine hydrochloride were added to a suspension of 8.15 g (23.0 mmoles) of 3-(2,4,6-trifluorophenyl)-4-(1-naphthyl)furan-2,5-dione in 60 ml of pyridine anhydrified on sieves. The mixture was left under stirring at reflux temperature for 2 hours.

After control in TLC and LC-MS, the solvent was removed at reduced pressure, water and ethyl acetate were added to the mixture, and the phases were then separated; the aqueous phase was re-extracted twice with ethyl acetate. The organic phases were joined and washed with water and a saturated solution of sodium chloride.

After anhydrification on sodium sulfate, filtration and evaporation of the solvent at reduced pressure, 9.1 g of yellow solid were obtained. The raw product was purified on a heptane:ethyl acetate 7:3 column, obtaining 7.3 g (20.6 mmoles) of the desired product as a yellow solid. Yield 90%

LC-MS [M+H]=369 d) Preparation of 1-methanesulfonyloxy-3-(2,4,6-trifluorophenyl)-4-(1-naphthyl)-1H-pyrrole-2,5-dione [Compound Having General Formula (I)]

3.0 ml (21.6 mmoles) of triethylamine were added to a suspension of 7.6 g (20.6 mmoles) of 1-hydroxy-3-(2,4,6-trifluorophenyl)-4-(1-naphthyl)-1H-pyrrole-2,5-dione in 40 ml of dichloromethane, and 1.68 ml (21.6 mmoles) of mesyl chloride diluted in 10 ml of dichloromethane were subsequently added dropwise on an ice bath. The mixture was left under stirring at room temperature for 2 hours.

After control in TLC and LC-MS, water and ethyl acetate were added to the mixture, and the phases were then separated; the aqueous phase was re-extracted twice with dichloromethane. The organic phases were joined and washed with water and a saturated solution of sodium chloride.

After anhydrification on sodium sulfate, filtration and evaporation of the solvent at reduced pressure, 11 g of a yellow oil were obtained, which tends to solidify. The raw product thus obtained was purified on a chromatographic column ($SiO_2$ heptane:ethyl acetate 8:2), obtaining 8.3 g (18.5 mmoles) of the desired product as a yellow solid. Yield 90%

LC-MS [M+H]=447

Example 6

Preparation of 1-hydroxy-3-(2-bromophenyl)-4-(6-methoxy-naphth-2-yl)furan-2,5-dione [Compound Nr. 18]

a) Preparation of 3-(2-bromophenyl)-4-(6-methoxy-naphth-2-yl)furan-2,5-dione [Anhydride Having General Formula (II)]

A mixture of 5.47 g of sodium salt of 6-methoxy-2-naphthylacetic acid (obtained from 5 g of 6-methoxy-2-naphthyl acetic acid and 0.93 g of sodium hydroxide in 21 ml of water) and 5.27 g of 2-bromophenylglyoxylic acid obtained as described in Example 1 a), in 48 g of acetic anhydride, was heated to reflux temperature for 2 hours.

After cooling and evaporation of most of the acetic anhydride, an extraction with water and ethyl acetate was effected (100 ml×2 times). The organic phases were joined, washed with water (150 ml×3 times), anhydrified with sodium sulfate and concentrated at reduced pressure.

The raw product obtained was purified by cold washing in hexane (50 ml), and was then filtered to give 7.5 g of the desired product.

GC-MS: 409 [M$^+$]

b) Preparation of 3-(2-bromophenyl)-4-(6-methoxy-naphth-2-yl)-1H-pyrrole-2,5-dione [Compound Having General Formula (I)]

A mixture of 7.5 g di 3-(2-bromophenyl)-4-(6-methoxy-naphth-2-yl)-furan-2,5-dione and 2.57 g of hydroxylamine hydrochloride, in 60 ml of pyridine, was heated to reflux temperature for 2 hours.

After cooling and evaporation of most of the pyridine, an extraction with water and ethyl acetate was effected. The organic phases were further washed with water and then anhydrified on sodium sulfate.

After evaporation of the solvent, 8.2 g of raw product were obtained which was purified by cold washing with a mixture of hexane:ethyl ether (300 ml).

After filtration, 6.87 g of the desired product were obtained.

GC-MS: 424 [M$^+$]

Example 7

Preparation of 1-acetyloxy-3-(2-bromophenyl)-4-(1-naphthyl)-1H-pyrrole-2,5-dione [Compound Nr. 11]

a) Preparation of 3-(2-bromophenyl)-4-(1-naphthyl)furan-2,5-dione [Anhydride Having General Formula (II)]

A suspension under nitrogen of 3.7 g (16.5 mmoles) of potassium 1-naphthylacetate and 3.78 g (16.5 mmoles) of 2-bromophenylglyoxylic acid obtained as described in Example 1 a) in 25 ml of acetic anhydride was heated under stirring to reflux temperature for 2 hours.

The reaction trend was controlled in TLC and in GC-MS. The acetic anhydride was removed at reduced pressure, water and ethyl acetate were added to the mixture, and the phases were then separated; the aqueous phase was re-extracted twice with ethyl acetate. The organic phases were joined and washed with water and a saturated solution of sodium chloride.

After anhydrification on sodium sulfate, filtration and evaporation of the solvent at reduced pressure, 5.61 g of the desired product (14.8 mmoles) were obtained, as a yellow solid. Yield 90%

LC-MS [M+H]=380 b) Preparation of 1-hydroxy-3-(2-bromophenyl)-4-(1-naphthyl)-1H-pyrrole-2,5-dione [N-hydroxyimide Having General Formula (III)]

1.85 g (26.7 mmoles) of hydroxylamine hydrochloride are added to a suspension of 5.04 g (13.3 mmoles) of 3-(2-bromophenyl)-4-(1-naphthyl)furan-2,5-dione in 25 ml of anhydrous pyridine (anhydrified on sieves).

After control in TLC and LC-MS, the solvent was removed at reduced pressure, water and ethyl acetate were added to the mixture, and the phases were then separated; the aqueous phase was re-extracted twice with ethyl acetate. The organic phases were joined and washed with water and a saturated solution of sodium chloride.

After anhydrification on sodium sulfate, filtration and evaporation of the solvent at reduced pressure, 5.62 g of a yellow oil were obtained, which tends to solidify. The raw product thus obtained was ground with a mixture of ethyl ether and heptane, filtered and dried in air, obtaining 4.45 g (11.3 mmoles) of the desired product as a yellow solid. Yield 85%

LC-MS [M+H]=395 c) Preparation of 1-acetyloxy-3-(2-bromophenyl)-4-(1-naphthyl)-1H-pyrrole-2,5-dione [Compound Having General Formula (I)]

1.65 ml (11.9 mmoles) of triethylamine were added to a suspension of 4.45 g (11.3 mmoles) of 1-hydroxy-3-(2-bromophenyl)-4-(1-naphthyl)-1H-pyrrole-2,5-dione in 20 ml of dichloromethane, and 0.85 ml (21.4 mmoles) of acetyl chloride diluted in 5 ml of dichloromethane were subsequently added dropwise on an ice bath. The mixture was left under stirring at room temperature for 2 hours.

After control in TLC and LC-MS, water and dichloromethane were added to the mixture, and the phases were then separated; the aqueous phase was re-extracted twice with dichloromethane. The organic phases were joined and washed with water and a saturated solution of sodium chloride.

After anhydrification on sodium sulfate, filtration and evaporation of the solvent at reduced pressure, 5.2 g of a yellow oil were obtained, which tends to solidify. The raw product thus obtained was purified on a chromatographic column (SiO$_2$ heptane:ethyl acetate 8:2), obtaining 4.66 g (10.7 mmoles) of the desired product as a yellow solid. Yield 95%

LC-MS [M+H]=437

Example 8

Determination of the Preventive Activity (7 Days) of Compounds Having Formula (I) Against *Plasmopara viticola* on Vines Leaves of vine plants, grown in pots, in a conditioned environment (20±1° C., 70% of R.H.), were treated by spraying both sides with the products under examination.

7 days after the treatment, the plants were inoculated with an aqueous suspension of spores of *Plasmopara viticola* (200,000 spores/cc) by spraying on both sides of the leaves with a compressed air gun.

After remaining 24 hours in a humidity saturated environment, at 21° C., the plants were transferred for the incubation period (7 days) to a conditioned environment at 70% R.H. and at 24° C.

After this period, the external symptoms of the pathogen appeared and it was consequently possible to proceed with a visual evaluation of the intensity of the infection.

The fungicidal activity is expressed as a reduction percentage, with respect to non-treated seedlings, in the area of the leaves affected by the disease (100=total effectiveness, 0=zero effectiveness).

Table 2 indicates the results obtained for the compounds tested, compared with the reference product Mancozeb (polymeric complex of manganese ethylenebisdithiocarbamate with zinc salt).

TABLE 2

| Compound Nr. | Dose (ppm) | Effectiveness (%) |
|---|---|---|
| 1 | 500 | 98 |
|   | 125 | 92 |
| 2 | 500 | 97 |
|   | 125 | 91 |
| 3 | 500 | 99 |
|   | 125 | 86 |
| 5 | 500 | 95 |
|   | 125 | 86 |
| 11 | 500 | 92 |
|   | 125 | 82 |
| 12 | 500 | 93 |
|   | 125 | 91 |
| 13 | 500 | 97 |
|   | 125 | 89 |
| Mancozeb | 500 | 96 |
|   | 125 | 78 |

As can be seen, the compounds according to the present invention show a high fungicidal activity, completely similar to that of the reference product Mancozeb at the same doses.

Example 9

Determination of the Preventive Activity (7 Days) of Compounds Having Formula (I) Against *Uromyces appendiculatus* on Beans Leaves of bean plants, grown in pots, in a conditioned environment (20±1° C., 70% of R.H.), were treated by spraying both sides with the products under examination.

7 days after the treatment, the plants were inoculated with an aqueous suspension of spores of *Uromyces appendiculatus* (200,000 spores/cc) by spraying on both sides of the leaves with a compressed air gun.

After remaining 24 hours in a humidity saturated environment, at 21° C., the plants were transferred for the incubation period (7 days) to a conditioned environment at 70% R.H. and at 24° C.

After this period, the external symptoms of the pathogen appeared and it was consequently possible to proceed with a visual evaluation of the intensity of the infection.

The fungicidal activity is expressed as a reduction percentage, with respect to non-treated seedlings, in the area of the leaves affected by the disease (100=total effectiveness, 0=zero effectiveness).

Table 3 indicates the results obtained for the compounds tested, compared with the reference product Domark® (Tetraconazole).

TABLE 3

| Compound Nr. | Dose (ppm) | Effectiveness (%) |
|---|---|---|
| 2 | 500 | 94 |
|   | 125 | 83 |
| 3 | 500 | 93 |
|   | 125 | 84 |
| 4 | 500 | 92 |
|   | 125 | 88 |
| 5 | 500 | 94 |
|   | 125 | 88 |
| 7 | 500 | 96 |
|   | 125 | 86 |
| 8 | 500 | 95 |
|   | 125 | 93 |
| 9 | 500 | 92 |
|   | 125 | 80 |
| 11 | 500 | 95 |
|   | 125 | 80 |
| 12 | 500 | 98 |
|   | 125 | 83 |
| 13 | 500 | 92 |
|   | 125 | 81 |
| Domark ® | 30 | 96 |

As can be seen, the compounds according to the present invention show a high fungicidal activity, completely similar to that of the reference product Domark®.

The invention claimed is:

1. N-substituted pyrrole-2,5-diones having formula (I):

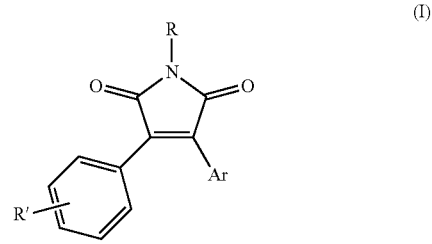

wherein:
R represents a group selected from the group consisting of —OR$_1$, —NHR$_2$, —NR$_3$R$_4$, —SO$_2$R$_5$ and —Si(R$_6$)$_3$;
Ar represents an aryl group selected from the group consisting of 1-naphthyl and 2-naphthyl, optionally substituted by one or more R" groups;
R$_1$ represents a group selected from the group consisting of a hydrogen atom, —C(O)R$_7$, —SO$_2$R$_8$ and —COOR$_9$;
R$_2$, R$_3$ and R$_4$ independently represent a group selected from the group consisting of C$_1$-C$_6$ alkyl, C$_3$-C$_6$ cycloalkyl, C$_1$-C$_6$ haloalkyl, C$_6$-C$_{12}$ alkylaryl, —C(O)R$_7$, —SO$_2$R$_8$ and —COOR$_9$;
R$_5$, R$_6$, R$_7$, R$_8$ and R$_9$ independently represent a group selected from the group consisting of C$_1$-C$_6$ alkyl, C$_3$-C$_6$ cycloalkyl, C$_1$-C$_6$ haloalkyl, and C$_6$-C$_{12}$ aryl, said aryl groups being optionally substituted by one or more groups selected from the group consisting of C$_1$-C$_6$ alkyl and halogen atoms;
R' and R" independently represent one or more groups selected from the group consisting of a hydrogen atom, a halogen atom, C$_1$-C$_6$ alkyl, C$_1$-C$_6$ haloalkyl, C$_3$-C$_6$-cycloalkyl, C$_4$-C$_7$-cycloalkylalkyl, C$_1$-C$_6$-alkoxyl, C$_1$-C$_6$-haloalkoxyl, C$_1$-C$_6$-thioalkoxyl, C$_1$-C$_6$-thiohaloalkoxyl, C$_1$-C$_6$-alkylsulfinyl, C$_1$-C$_6$-alkylsulfonyl, C$_1$-C$_6$-alkoxycarbonyl, C$_3$-C$_6$-cycloalkoxycarbonyl, amino, N—C$_1$-C$_6$-alkylamino, N,N—C$_2$-C$_{12}$-dialkylamino, N—C$_1$-C$_6$ alkoxycarbonyl-amino, N—C$_3$-C$_6$-cycloalkylamino, N,N—C$_6$-C$_{12}$-dicycloalkylamino, N—C$_3$-C$_6$-cycloalkoxycarbonyl-amino, C$_1$-C$_6$-alkylamino-carbonyl, C$_3$-C$_6$-cycloalkylaminocarbonyl, NR$_1$R$_2$CONR$_1$—, formyl, carboxyl, and cyano;
excluding compounds wherein:
R is —OSO$_2$CH$_3$, Ar is 1-naphthyl, R' and R" are H;
R is —OSO$_2$CF$_3$, Ar is 1-naphthyl, R' and R" are H;
R is —OH, R' is 3,4,5-OMe, Ar is 2-naphthyl, and R" is H.

2. The N-substituted pyrrole-2,5-diones having formula (I) according to claim 1, wherein R represents a group selected from the group consisting of —OR$_1$, —NHR$_2$, and —SO$_2$R$_5$;

Ar represents an aryl group selected from the group consisting of 1-naphthyl and 2-naphthyl, optionally substituted by one or more R" groups;

R$_1$ represents a group selected from the group consisting of a hydrogen atom, —C(O)R$_7$, —SO$_2$R$_8$ and —COOR$_9$;

R$_2$ represents a group selected from the group consisting of —C(O)R$_7$, —SO$_2$R$_8$ and —COOR$_9$;

R$_5$, R$_7$ and R$_8$ independently represent a group selected from the group consisting of C$_1$-C$_6$ alkyl, C$_3$-C$_6$ cycloalkyl, C$_1$-C$_6$ haloalkyl, and C$_6$-C$_{12}$ aryl, said aryl groups being optionally substituted by one or more groups selected from the group consisting of C$_1$-C$_6$ alkyl and halogen atoms;

R$_9$ represents a C$_1$-C$_6$ alkyl group;

R' and R" independently represent one or more groups selected from the group consisting of hydrogen, halogen, C$_1$-C$_6$ haloalkyl, C$_1$-C$_6$ alkoxyl, and C1-C$_6$ haloalkoxyl.

3. The N-substituted pyrrole-2,5-diones having formula (I) according to claim 1, selected from the following compounds:

| Compound Nr. | R | R' | R" | Ar |
| --- | --- | --- | --- | --- |
| 1 | OH | 2,4,6-F | H | 1-naphthyl |
| 2 | OH | 2-Br | H | 1-naphthyl |
| 3 | SO$_2$Me | H | H | 1-naphthyl |
| 4 | NH—COOEt | H | H | 1-naphthyl |
| 6 | OSO$_2$p-Tol | H | H | 1-naphthyl |
| 7 | SO$_2$—p-Tol | H | H | 1-naphthyl |
| 8 | NH—COOt-Bu | H | H | 1-naphthyl |
| 9 | OC(O)Ph | H | H | 1-naphthyl |
| 10 | NH—COOMe | H | H | 1-naphthyl |
| 11 | OC(O)Me | 2-Br | H | 1-naphthyl |
| 12 | OSO$_2$Me | 2-Br | H | 1-naphthyl |
| 13 | NH—COOEt | 2-Br | H | 1-naphthyl |
| 14 | NH—COOt-Bu | 2-Br | H | 1-naphthyl |
| 15 | OSO$_2$Me | 2,4,6-F | H | 1-naphthyl |
| 16 | OC(O)Me | 2,4,6-F | H | 2-naphthyl |
| 17 | OH | 2-Br | 4-F | 1-naphthyl |
| 18 | OH | 2-Br | 6-OMe | 2-naphthyl. |

4. A method for the control of phytopathogenic fungi in agricultural crops comprising a step of using N-substituted pyrrole-2,5-diones having formula (I):

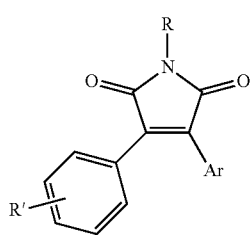

wherein:

R represents a group selected from the group consisting of —OR$_1$, —NHR$_2$, —NR$_3$R$_4$, —SO$_2$R$_5$ and —Si(R$_6$)$_3$;

Ar represents an aryl group selected from the group consisting of 1-naphthyl and 2-naphthyl, optionally substituted by one or more R" groups;

R$_1$ represents a group selected from the group consisting of a hydrogen atom, —C(O)R$_7$, —SO$_2$R$_8$ and —COOR$_9$;

R$_2$, R$_3$ and R$_4$ independently represent a group selected from the group consisting of C$_1$-C$_6$ alkyl, C$_3$-C$_6$ cycloalkyl, C$_1$-C$_6$ haloalkyl, C$_6$-C$_{12}$ alkylaryl, —C(O)R$_7$, —SO$_2$R$_8$ and —COOR$_9$;

R$_5$, R$_6$, R$_7$, R$_8$ and R$_9$ independently represent a group selected from the group consisting of C$_1$-C$_6$ alkyl, C$_3$-C$_6$ cycloalkyl, C$_1$-C$_6$ haloalkyl, C$_6$-C$_{12}$ aryl, said aryl groups being optionally substituted by one or more groups selected from C$_1$-C$_6$ alkyl and halogen atoms;

R' and R" independently represent one or more groups selected from the group consisting of a hydrogen atom, a halogen atom, C$_1$-C$_6$ alkyl, C$_1$-C$_6$ haloalkyl, C$_3$-C$_6$-cycloalkyl, C$_4$-C$_7$-cycloalkylalkyl, C$_1$-C$_6$-alkoxyl, C$_1$-C$_6$-haloalkoxyl, C$_1$-C$_6$-thioalkoxyl, C$_1$-C$_6$-thiohaloalkoxyl, C$_1$-C$_6$-alkylsulfinyl, C$_1$-C$_6$-alkylsulfonyl, C$_1$-C$_6$-alkoxycarbonyl, C$_3$-C$_6$-cycloalkoxycarbonyl, amino, N—C$_1$-C$_6$-alkylamino, N,N—C$_2$-C$_{12}$-dialkylamino, N—C$_1$-C$_6$-alkoxycarbonylamino, N—C$_3$-C$_6$-cycloalkylamino, N,N—C$_6$-C$_{12}$-dicycloalkylamino, N—C$_3$-C$_6$-cycloalkoxycarbonyl-amino, C$_1$-C$_6$-alkylaminocarbonyl, C$_3$-C$_6$-cycloalkylaminocarbonyl, NR$_1$R$_2$CONR$_1$—, formyl, carboxyl, and cyano.

5. The method according to claim 4, wherein

R represents a group selected from the group consisting of —OR$_1$, —NHR$_2$, and —SO$_2$R$_5$;

Ar represents an aryl group selected from the group consisting of 1-naphthyl and 2-naphthyl, optionally substituted by one or more R" groups;

R$_1$ represents a group selected from the group consisting of a hydrogen atom, —C(O)R$_7$, —SO$_2$R$_8$ and —COOR$_9$;

R$_2$ represents a group selected from the group consisting of —C(O)R$_7$, —SO$_2$R$_8$ and —COOR$_9$;

R$_5$, R$_7$ and R$_8$ independently represent a group selected from C$_1$-C$_6$ alkyl, C$_3$-C$_6$ cycloalkyl, C$_1$-C$_6$ haloalkyl, and C$_6$-C$_{12}$ aryl, said aryl groups being optionally substituted by one or more groups selected from the group consisting of C$_1$-C$_6$ alkyl and halogen atoms;

R$_9$ represents a C$_1$-C$_6$ alkyl group;

R' and R" independently represent one or more groups selected from the group consisting of hydrogen, halogen, C$_1$-C$_6$ haloalkyl, C$_1$-C$_6$ alkoxyl, and C$_1$-C$_6$ haloalkoxyl.

6. The method according to claim 4, wherein the compounds having formula (I) are selected from:

| Compound Nr. | R | R' | R" | Ar |
| --- | --- | --- | --- | --- |
| 1 | OH | 2,4,6-F | H | 1-naphthyl |
| 2 | OH | 2-Br | H | 1-naphthyl |
| 3 | SO$_2$Me | H | H | 1-naphthyl |
| 4 | NH—COOEt | H | H | 1-naphthyl |
| 6 | OSO$_2$p-Tol | H | H | 1-naphthyl |
| 7 | SO$_2$—p-Tol | H | H | 1-naphthyl |
| 8 | NH—COOt-Bu | H | H | 1-naphthyl |
| 9 | OC(O)Ph | H | H | 1-naphthyl |
| 10 | NH—COOMe | H | H | 1-naphthyl |
| 11 | OC(O)Me | 2-Br | H | 1-naphthyl |
| 12 | OSO$_2$Me | 2-Br | H | 1-naphthyl |
| 13 | NH—COOEt | 2-Br | H | 1-naphthyl |
| 14 | NH—COOt-Bu | 2-Br | H | 1-naphthyl |
| 15 | OSO$_2$Me | 2,4,6-F | H | 1-naphthyl |
| 16 | OC(O)Me | 2,4,6-F | H | 2-naphthyl |
| 17 | OH | 2-Br | 4-F | 1-naphthyl |
| 18 | OH | 2-Br | 6-OMe | 2-naphthyl. |

7. The method according to claim 4, of both a curative and preventive nature, wherein the phytopathogenic fungi comprise one or more of the following species: Basidiomycetes, Ascomycetes, Deuteromycetes or imperfect fungi, Oomycetes: *Puccinia* spp., *Ustilago* spp., *Tilletia* spp., *Uromyces* spp., *Phakopsora* spp., *Rhizoctonia* spp., *Erysiphe* spp., *Sphaerotheca* spp., *Podosphaera* spp., *Uncinula* spp., *Helminthosporium* spp., *Rhynchosporium* spp., *Pyrenophora* spp., *Monilinia* spp., *Sclerotinia* spp., *Septoria* spp. (*Mycosphaerella* spp.), *Venturia* spp., *Botrytis* spp., *Alternaria* spp., *Fusarium* spp., *Cercospora* spp., *Cercosporella herpotrichoides, Colletotrichum* spp., *Pyricularia oryzae, Sclerotium* spp., *Phytophthora* spp., *Pythium* spp., *Plasmopara viticola, Peronospora* spp., *Pseudoperonospora cubensis, Bremia lactucae*, in agricultural crops selected from the group consisting of cereals, fruit, citrus fruit, legumes, vegetables, cucurbits, oleaginous plants, tobacco, coffee, tea, cocoa, sugar beet, sugar cane, cotton, and combinations thereof.

8. An agronomical fungicidal compound comprising:
one or more compounds having formula (I) according to claim 1;
and one or more agronomically acceptable co-formulants, selected from the group consisting of a solvent, solid, liquid or liquefied diluent, optionally one or more surfactants, other agronomically acceptable co-formulants, and combinations thereof.

9. An agronomical fungicidal compound comprising one or more compounds having formula (I) according to claim 1, and at least a second active principle selected from the group consisting of insecticides, acaricides, nematicides, herbicides, fungicides other than those having formula (I), bactericides, fertilizers, biostimulants, and combinations thereof.

10. A method comprising using the agronomical compound according to claim 8 for the control of phytopathogenic fungi in agricultural crops.

11. A method for controlling phytopathogenic fungi in agricultural crops, comprising a step of applying effective and non-phytotoxic doses of the compound having formula (I) according to claim 1, to an agricultural crop in a quantity ranging from 500 g to 800 g per hectare of said agricultural crop.

12. The fungicidal agronomical compound of claim 8 in the form of dry powders, wettable powders, emulsifiable concentrates, microemulsions, pastes, granulates, solutions, suspensions, fumigants, and mixtures thereof.

13. The method of claim 10 wherein the phytopathogenic fungi comprise one or more of the following: Basidiomycetes, Ascomycetes, Deuteromycetes or imperfect fungi, Oomycetes: *Puccinia* spp., *Ustilago* spp., *Tilletia* spp., *Uromyces* spp., *Phakopsora* spp., *Rhizoctonia* spp., *Erysiphe* spp., *Sphaerotheca* spp., *Podosphaera* spp., *Uncinula* spp., *Helminthosporium* spp., *Rhynchosporium* spp., *Pyrenophora* spp., *Monilinia* spp., *Sclerotinia* spp., *Septoria* spp. (*Mycosphaerella* spp.), *Venturia* spp., *Botrytis* spp., *Alternaria* spp., *Fusarium* spp., *Cercospora* spp., *Cercosporella herpotrichoides, Colletotrichum* spp., *Pyricularia oryzae, Sclerotium* spp., *Phytophthora* spp., *Pythium* spp., *Plasmopara viticola, Peronospora* spp., *Pseudoperonospora cubensis, Bremia lactucae*, in agricultural crops selected from the group consisting of cereals, fruit, citrus fruit, legumes, vegetables, cucurbits, oleaginous plants, tobacco, coffee, tea, cocoa, sugar beet, sugar cane, cotton, and combinations thereof.

* * * * *